US006518417B1

(12) United States Patent
Sczakiel et al.

(10) Patent No.: US 6,518,417 B1
(45) Date of Patent: Feb. 11, 2003

(54) ANTISENSE NUCLEIC ACIDS TARGETING HBV

(76) Inventors: Georg Sczakiel, Beintweg 9a, D-69181 Leimen (DE); Volker Patzel, Jahnstrasse 26, GP221 Dossenheim (DE)

( * ) Notice: Subject to any disclaimer, the term of this patent is extended or adjusted under 35 U.S.C. 154(b) by 0 days.

(21) Appl. No.: 09/446,289

(22) PCT Filed: Jun. 16, 1998

(86) PCT No.: PCT/EP98/03632

§ 371 (c)(1),
(2), (4) Date: Apr. 13, 2000

(87) PCT Pub. No.: WO98/58055

PCT Pub. Date: Dec. 23, 1998

(30) Foreign Application Priority Data

Jun. 18, 1997 (DE) .......................... 197 25 803

(51) Int. Cl.[7] .................... C07H 21/04; C07H 21/02; C12Q 1/68; C12P 19/34; C12N 15/63
(52) U.S. Cl. .................... 536/24.5; 435/6; 435/91.1; 435/455; 435/375; 536/23.1
(58) Field of Search .................. 435/6, 91.1, 455, 435/366; 514/44; 536/23.1, 24.5

(56) References Cited

U.S. PATENT DOCUMENTS 5,981,274 A * 11/1999 Tyrrell et al. ............. 435/320.1

FOREIGN PATENT DOCUMENTS

| GB | WO 96/03152 | 2/1996 | .......... A61K/48/00 |
| WO | WO 90/13667 | 11/1990 | ............ C12Q/1/68 |
| WO | WO 97/03211 | 1/1997 | ............ C12Q/1/68 |

OTHER PUBLICATIONS

Andrea D. Branch, A good antiense molecule is hard to find, ITBS 23—Feb. 1998, pp. 45–50.*
Stanley T. Crook, Antisense Research and Application, pp. 1–50.*
Giorgio Palu', In pursuit of new developments for gene therapy of human diseases, Journal of Biotechnology 68 (1999) pp. 1–13.*
Karola Rittner et al., In vitro selection fast–hybridizing and effective antisense RNAs directed against the human immunodeficiency virus type 1, Nucleic Acids Research 1993, vol. 21, No. 6 pp. 1381–1387.*
John J. Rossi et al., Introductory Remarks on the Gereral Application of Antisense RNAs and Ribozymes, A Companion to Methods in Enzymology 5, pp. 1–5 (1993).*
Natalie Milner et al., Selecting effective antisense reagents on combinatorial oligonucleotide arrays, NATURE BIOTECHNOLOGY vol. 15, Jun. 1997.*
Karen Pihl–Carey et al., Isis To Restructure As Crohn's Disease Drug Fails In Phase III, BIOWORLD TODAY, vol. 10, No. 239, Dec. 16, 1999 pp. 1–2*
Oh et al., Inhibition of Hepatitis B Virus Expression by Antisense Oligodeoxyribonucleotides, Korean J. Boichem (1993) 25: 113–118.
Rittner et al., In Vitro Selection of Fast–Hybridizing and Effective Antisense RNAs Directed Against the Human Immunodeficiency Virus Type 1, Nucleic Acids Research (1993) 21: 1381–1387.
Patzel et al., Theoretical and Experimental Selection Parameters for HBV–Directed Antisense RNA Are Related to Increased RNA–RNA Annealing, Biol. Chem. 378:539–543 (1997).
Patzel and Sczakiel, Theoretical Design of Antisense RNA Structuress Substantially Improves Annealing Kinetics and Efficacy in Human Cells, Nature Biotechnology 16: 64–68 (1998).
Sczakiel, The Design of Antisense RNA, Antisense & Nucleic Acid Drug Development 7:439–444 (1997).

* cited by examiner

Primary Examiner—Andrew Wang
Assistant Examiner—Jane Zara
(74) Attorney, Agent, or Firm—Womble Carlyle Sandridge & Rice, PLLC

(57) ABSTRACT

The present invention concerns antisense nucleic acids which are directed against specific sequences of RNA molecules originating from HBV and vectors and host cells containing these antisense nucleic acids.

2 Claims, 5 Drawing Sheets

SEQUENCE LISTING

```
<160> NUMBER OF SEQ ID NOS: 121

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 1
gcgagggagt tcttcttcta                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 2 gatccccta gaaaattg                                                       18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 3
ggatcggcag aggagccaca aa                                                 22

<210> SEQ ID NO 4
<211> LENGTH: 56
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 4
gaauacucaa gcuaugcauc caacgcguug ggagcucucc ggauccccu agaaaa             56

<210> SEQ ID NO 5
```

```
<211> LENGTH: 57
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 5
gaauacucaa gcuaugcauc caacgcguug ggagcucucc ggaucccccu agaaaau            57

<210> SEQ ID NO 6
<211> LENGTH: 58
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 6
gaauacucaa gcuaugcauc caacgcguug ggagcucucc ggaucccccu agaaaauu           58

<210> SEQ ID NO 7
<211> LENGTH: 59
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 7
gaauacucaa gcuaugcauc caacgcguug ggagcucucc ggaucccccu agaaaauug          59

<210> SEQ ID NO 8
<211> LENGTH: 60
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 8
gaauacucaa gcuaugcauc caacgcguug ggagcucucc ggaucccccu agaaaauuga         60

<210> SEQ ID NO 9
<211> LENGTH: 77
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 9
gaauacucaa gcuaugcauc caacgcguug ggagcucucc ggaucccccu agaaaauuga         60
gagaagucca ccacgag                                                       77

<210> SEQ ID NO 10
<211> LENGTH: 78
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 10
gaauacucaa gcuaugcauc caacgcguug ggagcucucc ggaucccccu agaaaauuga         60
gagaagucca ccacgagu                                                      78
```

<210> SEQ ID NO 11
<211> LENGTH: 79
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 11
gaauacucaa gcuaugcauc caacgcguug ggagcucucc ggauccccu agaaaauuga    60 gagaagucca ccacgaguc                                                79

<210> SEQ ID NO 12
<211> LENGTH: 80
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 12
gaauacucaa gcuaugcauc caacgcguug ggagcucucc ggauccccu agaaaauuga    60 gagaagucca ccacgagucu                                               80

<210> SEQ ID NO 13
<211> LENGTH: 81
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 13
gaauacucaa gcuaugcauc caacgcguug ggagcucucc ggauccccu agaaaauuga    60 gagaagucca ccacgagucu a                                             81

<210> SEQ ID NO 14
<211> LENGTH: 82
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 14
gaauacucaa gcuaugcauc caacgcguug ggagcucucc ggauccccu agaaaauuga    60 gagaagucca ccacgagucu ag                                            82

<210> SEQ ID NO 15
<211> LENGTH: 83
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 15
gaauacucaa gcuaugcauc caacgcguug ggagcucucc ggauccccu agaaaauuga    60 gagaagucca ccacgagucu aga                                           83

<210> SEQ ID NO 16

```
<211> LENGTH: 84
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 16
gaauacucaa gcuaugcauc caacgcguug ggagcucucc ggauccccu agaaaauuga      60 gagaagucca ccacgagucu agac                                            84

<210> SEQ ID NO 17
<211> LENGTH: 101
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 17
gaauacucaa gcuaugcauc caacgcguug ggagcucucc ggauccccu agaaaauuga      60 gagaagucca ccacgagucu agacucugcg guauugugag g                        101

<210> SEQ ID NO 18
<211> LENGTH: 102
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 18
gaauacucaa gcuaugcauc caacgcguug ggagcucucc ggauccccu agaaaauuga      60 gagaagucca ccacgagucu agacucugcg guauugugag ga                       102

<210> SEQ ID NO 19
<211> LENGTH: 103
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 19
gaauacucaa gcuaugcauc caacgcguug ggagcucucc ggauccccu agaaaauuga      60 gagaagucca ccacgagucu agacucugcg guauugugag gau                      103

<210> SEQ ID NO 20
<211> LENGTH: 104
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 20
gaauacucaa gcuaugcauc caacgcguug ggagcucucc ggauccccu agaaaauuga      60 gagaagucca ccacgagucu agacucugcg guauugugag gauu                     104

<210> SEQ ID NO 21
<211> LENGTH: 113
<212> TYPE: RNA
<213> ORGANISM: Artificial Sequence
<220> FEATURE:
```

-continued

```
<223> OTHER INFORMATION: Description of Artificial Sequence: antisense
      nucleic acid against RNA originating from HBV

<400> SEQUENCE: 21
gaauacucaa gcuaugcauc caacgcguug ggagcucucc ggauccccu agaaaauuga      60 gagaagucca ccacgagucu agacucugcg guauugugag gauucuuguc aac           113

<210> SEQ ID NO 22
<211> LENGTH: 114
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 22
gaauacucaa gcuaugcauc caacgcguug ggagcucucc ggauccccu agaaaauuga      60 gagaagucca ccacgagucu agacucugcg guauugugag gauucuuguc aaca          114

<210> SEQ ID NO 23
<211> LENGTH: 115
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 23
gaauacucaa gcuaugcauc caacgcguug ggagcucucc ggauccccu agaaaauuga      60 gagaagucca ccacgagucu agacucugcg guauugugag gauucuuguc aacaa         115

<210> SEQ ID NO 24
<211> LENGTH: 116
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 24
gaauacucaa gcuaugcauc caacgcguug ggagcucucc ggauccccu agaaaauuga      60 gagaagucca ccacgagucu agacucugcg guauugugag gauucuuguc aacaag        116

<210> SEQ ID NO 25
<211> LENGTH: 117
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 25
gaauacucaa gcuaugcauc caacgcguug ggagcucucc ggauccccu agaaaauuga      60 gagaagucca ccacgagucu agacucugcg guauugugag gauucuuguc aacaaga       117

<210> SEQ ID NO 26
<211> LENGTH: 137
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 26
```
gaauacucaa gcuaugcauc caacgcguug ggagcucucc ggauccccu agaaaauuga        60 gagaagucca ccacgagucu agacucugcg guauugugag gauucuuguc aacaagaaaa       120
accccgccug uaacacg                                                      137

<210> SEQ ID NO 27
<211> LENGTH: 138
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 27
gaauacucaa gcuaugcauc caacgcguug ggagcucucc ggauccccu agaaaauuga        60 gagaagucca ccacgagucu agacucugcg guauugugag gauucuuguc aacaagaaaa       120
accccgccug uaacacga                                                     138

<210> SEQ ID NO 28
<211> LENGTH: 139
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 28
gaauacucaa gcuaugcauc caacgcguug ggagcucucc ggauccccu agaaaauuga        60 gagaagucca ccacgagucu agacucugcg guauugugag gauucuuguc aacaagaaaa       120
accccgccug uaacacgag                                                    139

<210> SEQ ID NO 29
<211> LENGTH: 140
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 29
gaauacucaa gcuaugcauc caacgcguug ggagcucucc ggauccccu agaaaauuga        60 gagaagucca ccacgagucu agacucugcg guauugugag gauucuuguc aacaagaaaa       120
accccgccug uaacacgagc                                                   140

<210> SEQ ID NO 30
<211> LENGTH: 149
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 30
gaauacucaa gcuaugcauc caacgcguug ggagcucucc ggauccccu agaaaauuga        60 gagaagucca ccacgagucu agacucugcg guauugugag gauucuuguc aacaagaaaa       120
accccgccug uaacacgagc aggguccu                                          149

<210> SEQ ID NO 31
<211> LENGTH: 150
<212> TYPE: RNA

<210> SEQ ID NO 31
<211> LENGTH: 150
<212> TYPE: RNA
<213> ORGANISM: Artificial Sequence
<220> FEATURE:
<223> OTHER INFORMATION: Description of Artificial Sequence: antisense
    nucleic acid against RNA originating from HBV

<400> SEQUENCE: 31
gaauacucaa gcuaugcauc caacgcguug ggagcucucc ggauccccu agaaaauuga      60 gagaagucca ccacgagucu agacucugcg guauugugag gauucuuguc aacaagaaaa    120
accccgccug uaacacgagc agggguccua                                      150

<210> SEQ ID NO 32
<211> LENGTH: 151
<212> TYPE: RNA
<213> ORGANISM: Artificial Sequence
<220> FEATURE:
<223> OTHER INFORMATION: Description of Artificial Sequence: antisense
    nucleic acid against RNA originating from HBV

<400> SEQUENCE: 32
gaauacucaa gcuaugcauc caacgcguug ggagcucucc ggauccccu agaaaauuga      60 gagaagucca ccacgagucu agacucugcg guauugugag gauucuuguc aacaagaaaa    120
accccgccug uaacacgagc agggguccua g                                    151

<210> SEQ ID NO 33
<211> LENGTH: 152
<212> TYPE: RNA
<213> ORGANISM: Artificial Sequence
<220> FEATURE:
<223> OTHER INFORMATION: Description of Artificial Sequence: antisense
    nucleic acid against RNA originating from HBV

<400> SEQUENCE: 33
gaauacucaa gcuaugcauc caacgcguug ggagcucucc ggauccccu agaaaauuga      60 gagaagucca ccacgagucu agacucugcg guauugugag gauucuuguc aacaagaaaa    120
accccgccug uaacacgagc agggguccua gg                                   152

<210> SEQ ID NO 34
<211> LENGTH: 153
<212> TYPE: RNA
<213> ORGANISM: Artificial Sequence
<220> FEATURE:
<223> OTHER INFORMATION: Description of Artificial Sequence: antisense
    nucleic acid against RNA originating from HBV

<400> SEQUENCE: 34
gaauacucaa gcuaugcauc caacgcguug ggagcucucc ggauccccu agaaaauuga      60 gagaagucca ccacgagucu agacucugcg guauugugag gauucuuguc aacaagaaaa    120
accccgccug uaacacgagc agggguccua gga                                  153

<210> SEQ ID NO 35
<211> LENGTH: 163
<212> TYPE: RNA
<213> ORGANISM: Artificial Sequence
<220> FEATURE:
<223> OTHER INFORMATION: Description of Artificial Sequence: antisense
    nucleic acid against RNA originating from HBV

<400> SEQUENCE: 35
gaauacucaa gcuaugcauc caacgcguug ggagcucucc ggauccccu agaaaauuga      60 gagaagucca ccacgagucu agacucugcg guauugugag gauucuuguc aacaagaaaa    120
accccgccug uaacacgagc aggggnccua ggaauccuga ugu        163

<210> SEQ ID NO 36
<211> LENGTH: 164
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 36
gaauacucaa gcuaugcauc caacgcguug ggagcucucc ggaucccccu agaaaauuga        60
gagaagucca ccacgagucu agacucugcg guauugugag gauucuuguc aacaagaaaa      120
accccgccug uaacacgagc aggggnccua ggaauccuga ugug       164

<210> SEQ ID NO 37
<211> LENGTH: 165
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 37
gaauacucaa gcuaugcauc caacgcguug ggagcucucc ggaucccccu agaaaauuga        60
gagaagucca ccacgagucu agacucugcg guauugugag gauucuuguc aacaagaaaa      120
accccgccug uaacacgagc aggggnccua ggaauccuga uguga      165

<210> SEQ ID NO 38
<211> LENGTH: 166
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 38
gaauacucaa gcuaugcauc caacgcguug ggagcucucc ggaucccccu agaaaauuga        60
gagaagucca ccacgagucu agacucugcg guauugugag gauucuuguc aacaagaaaa      120
accccgccug uaacacgagc aggggnccua ggaauccuga ugugau     166

<210> SEQ ID NO 39
<211> LENGTH: 167
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 39
gaauacucaa gcuaugcauc caacgcguug ggagcucucc ggaucccccu agaaaauuga        60
gagaagucca ccacgagucu agacucugcg guauugugag gauucuuguc aacaagaaaa      120
accccgccug uaacacgagc aggggnccua ggaauccuga ugugaug    167

<210> SEQ ID NO 40
<211> LENGTH: 168
<212> TYPE: RNA
<213> ORGANISM: Artificial Sequence
<220> FEATURE:
<223> OTHER INFORMATION: Description of Artificial Sequence: antisense
      nucleic acid against RNA originating from HBV -continued

<400> SEQUENCE: 40
gaauacucaa gcuaugcauc caacgcguug ggagcucucc ggauccccu agaaaauuga        60 gagaagucca ccacgagucu agacucugcg guauugugag gauucuuguc aacaagaaaa      120
accccgccug uaacacgagc aggguccua ggaauccuga ugugaugu                    168

<210> SEQ ID NO 41
<211> LENGTH: 217
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 41
gaauacucaa gcuaugcauc caacgcguug ggagcucucc ggauccccu agaaaauuga        60 gagaagucca ccacgagucu agacucugcg guauugugag gauucuuguc aacaagaaaa      120
accccgccug uaacacgagc aggguccua ggaauccuga ugugauguuc ccauguucg       180 ucacagdgguc cccaguccuc gcggagauug acgagau                              217

<210> SEQ ID NO 42
<211> LENGTH: 218
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 42
gaauacucaa gcuaugcauc caacgcguug ggagcucucc ggauccccu agaaaauuga        60 gagaagucca ccacgagucu agacucugcg guauugugag gauucuuguc aacaagaaaa      120
accccgccug uaacacgagc aggguccua ggaauccuga ugugauguuc ccauguucg       180 ucacagdgguc cccaguccuc gcggagauug acgagaug                             218

<210> SEQ ID NO 43
<211> LENGTH: 219
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 43
gaauacucaa gcuaugcauc caacgcguug ggagcucucc ggauccccu agaaaauuga        60 gagaagucca ccacgagucu agacucugcg guauugugag gauucuuguc aacaagaaaa      120
accccgccug uaacacgagc aggguccua ggaauccuga ugugauguuc ccauguucg       180 ucacagdgguc cccaguccuc gcggagauug acgagaugu                            219

<210> SEQ ID NO 44
<211> LENGTH: 220
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 44
gaauacucaa gcuaugcauc caacgcguug ggagcucucc ggauccccu agaaaauuga        60 gagaagucca ccacgagucu agacucugcg guauugugag gauucuuguc aacaagaaaa      120

```
accccgccug uaacacgagc aggggunccua ggaauccuga ugugauguuc uccauguucg    180
ucacaggguc cccaguccuc gcggagauug acgagaugug                           220
```

<210> SEQ ID NO 45
<211> LENGTH: 221
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 45

```
gaauacucaa gcuaugcauc caacgcguug ggagcucucc ggaucccccu agaaaauuga     60
gagaagucca ccacgagucu agacucugcg guauugugag gauucuuguc aacaagaaaa   120
accccgccug uaacacgagc aggggunccua ggaauccuga ugugauguuc uccauguucg   180
ucacaggguc cccaguccuc gcggagauug acgagaugug a                       221
```

<210> SEQ ID NO 46
<211> LENGTH: 222
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 46

```
gaauacucaa gcuaugcauc caacgcguug ggagcucucc ggaucccccu agaaaauuga     60
gagaagucca ccacgagucu agacucugcg guauugugag gauucuuguc aacaagaaaa   120
accccgccug uaacacgagc aggggunccua ggaauccuga ugugauguuc uccauguucg   180
ucacaggguc cccaguccuc gcggagauug acgagaugug ag                      222
```

<210> SEQ ID NO 47
<211> LENGTH: 223
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 47

```
gaauacucaa gcuaugcauc caacgcguug ggagcucucc ggaucccccu agaaaauuga     60
gagaagucca ccacgagucu agacucugcg guauugugag gauucuuguc aacaagaaaa   120
accccgccug uaacacgagc aggggunccua ggaauccuga ugugauguuc uccauguucg   180
ucacaggguc cccaguccuc gcggagauug acgagaugug aga                     223
```

<210> SEQ ID NO 48
<211> LENGTH: 224
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 48

```
gaauacucaa gcuaugcauc caacgcguug ggagcucucc ggaucccccu agaaaauuga     60
gagaagucca ccacgagucu agacucugcg guauugugag gauucuuguc aacaagaaaa   120
accccgccug uaacacgagc aggggunccua ggaauccuga ugugauguuc uccauguucg   180
```
ucacaggguc cccaguccuc gcggagauug acgagaugug agag         224

<210> SEQ ID NO 49
<211> LENGTH: 238
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 49
gaauacucaa gcuaugcauc caacgcguug ggagcucucc ggauccccu agaaaauuga         60 gagaagucca ccacgagucu agacucugcg guauugugag gauucuuguc aacaagaaaa      120
accccgccug uaacacgagc aggguccua ggaaccuga ugugauguuc ccauguucg         180 ucacaggguc cccaguccuc gcggagauug acgagaugug agaggcaaua uucggagc        238

<210> SEQ ID NO 50
<211> LENGTH: 239
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 50
gaauacucaa gcuaugcauc caacgcguug ggagcucucc ggauccccu agaaaauuga         60 gagaagucca ccacgagucu agacucugcg guauugugag gauucuuguc aacaagaaaa      120
accccgccug uaacacgagc aggguccua ggaaccuga ugugauguuc ccauguucg         180 ucacaggguc cccaguccuc gcggagauug acgagaugug agaggcaaua uucggagca       239

<210> SEQ ID NO 51
<211> LENGTH: 240
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 51
gaauacucaa gcuaugcauc caacgcguug ggagcucucc ggauccccu agaaaauuga         60 gagaagucca ccacgagucu agacucugcg guauugugag gauucuuguc aacaagaaaa      120
accccgccug uaacacgagc aggguccua ggaaccuga ugugauguuc ccauguucg         180 ucacaggguc cccaguccuc gcggagauug acgagaugug agaggcaaua uucggagcag      240

<210> SEQ ID NO 52
<211> LENGTH: 241
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 52
gaauacucaa gcuaugcauc caacgcguug ggagcucucc ggauccccu agaaaauuga         60 gagaagucca ccacgagucu agacucugcg guauugugag gauucuuguc aacaagaaaa      120
accccgccug uaacacgagc aggguccua ggaaccuga ugugauguuc ccauguucg         180 ucacaggguc cccaguccuc gcggagauug acgagaugug agaggcaaua uucggagcag      240
g                                                                      241

<210> SEQ ID NO 53
<211> LENGTH: 242
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 53
gaauacucaa gcuaugcauc caacgcguug ggagcucucc ggauccccu agaaaauuga      60 gagaagucca ccacgagucu agacucugcg guauugugag gauucuuguc aacaagaaaa   120
accccgccug uaacacgagc agggguccua ggaauccuga ugugauguuc uccauguucg   180
ucacaggguc cccagccuc gcggagauug acgagaugug agaggcaaua uucggagcag    240
gg                                                                  242

<210> SEQ ID NO 54
<211> LENGTH: 243
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 54
gaauacucaa gcuaugcauc caacgcguug ggagcucucc ggauccccu agaaaauuga      60 gagaagucca ccacgagucu agacucugcg guauugugag gauucuuguc aacaagaaaa   120
accccgccug uaacacgagc agggguccua ggaauccuga ugugauguuc uccauguucg   180
ucacaggguc cccagccuc gcggagauug acgagaugug agaggcaaua uucggagcag    240
ggu                                                                 243

<210> SEQ ID NO 55
<211> LENGTH: 244
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 55
gaauacucaa gcuaugcauc caacgcguug ggagcucucc ggauccccu agaaaauuga      60 gagaagucca ccacgagucu agacucugcg guauugugag gauucuuguc aacaagaaaa   120
accccgccug uaacacgagc agggguccua ggaauccuga ugugauguuc uccauguucg   180
ucacaggguc cccagccuc gcggagauug acgagaugug agaggcaaua uucggagcag    240
gguu                                                                244

<210> SEQ ID NO 56
<211> LENGTH: 245
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 56
gaauacucaa gcuaugcauc caacgcguug ggagcucucc ggauccccu agaaaauuga      60 gagaagucca ccacgagucu agacucugcg guauugugag gauucuuguc aacaagaaaa   120

-continued

```
accccgccug uaacacgagc aggggucuua ggaauccuga ugugauguuc uccauguucg      180 ucacagggguc cccaguccuc gcggagauug acgagaugug agaggcaaua uucggagcag     240
gguuu                                                                 245

<210> SEQ ID NO 57
<211> LENGTH: 246
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 57
gaauacucaa gcuaugcauc caacgcguug ggagcucucc ggauccccu agaaaauuga       60 gagaagucca ccacgagucu agacucugcg guauugugag gauucuuguc aacaagaaaa     120
accccgccug uaacacgagc aggggguccua ggaauccuga ugugauguuc uccauguucg    180 ucacagggguc cccaguccuc gcggagauug acgagaugug agaggcaaua uucggagcag    240
gguuua                                                                246

<210> SEQ ID NO 58
<211> LENGTH: 247
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 58
gaauacucaa gcuaugcauc caacgcguug ggagcucucc ggauccccu agaaaauuga       60 gagaagucca ccacgagucu agacucugcg guauugugag gauucuuguc aacaagaaaa     120
accccgccug uaacacgagc aggggguccua ggaauccuga ugugauguuc uccauguucg    180 ucacagggguc cccaguccuc gcggagauug acgagaugug agaggcaaua uucggagcag    240
gguuuac                                                               247

<210> SEQ ID NO 59
<211> LENGTH: 248
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 59
gaauacucaa gcuaugcauc caacgcguug ggagcucucc ggauccccu agaaaauuga       60 gagaagucca ccacgagucu agacucugcg guauugugag gauucuuguc aacaagaaaa     120
accccgccug uaacacgagc aggggguccua ggaauccuga ugugauguuc uccauguucg    180 ucacagggguc cccaguccuc gcggagauug acgagaugug agaggcaaua uucggagcag    240
gguuuacu                                                              248

<210> SEQ ID NO 60
<211> LENGTH: 59
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 60
```
gaauacucaa gcuaugcauc caacgcguug ggagcucucc ggaucggcag aggagccac        59

<210> SEQ ID NO 61
<211> LENGTH: 60
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 61
gaauacucaa gcuaugcauc caacgcguug ggagcucucc ggaucggcag aggagccaca       60

<210> SEQ ID NO 62
<211> LENGTH: 61
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 62
gaauacucaa gcuaugcauc caacgcguug ggagcucucc ggaucggcag aggagccaca       60
a                                                                      61

<210> SEQ ID NO 63
<211> LENGTH: 62
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 63
gaauacucaa gcuaugcauc caacgcguug ggagcucucc ggaucggcag aggagccaca       60
aa                                                                     62

<210> SEQ ID NO 64
<211> LENGTH: 63
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 64
gaauacucaa gcuaugcauc caacgcguug ggagcucucc ggaucggcag aggagccaca       60
aag                                                                    63

<210> SEQ ID NO 65
<211> LENGTH: 64
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 65
gaauacucaa gcuaugcauc caacgcguug ggagcucucc ggaucggcag aggagccaca       60
aagg                                                                   64

<210> SEQ ID NO 66
<211> LENGTH: 65

```
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 66
gaauacucaa gcuaugcauc caacgcguug ggagcucucc ggaucggcag aggagccaca    60
aaggu                                                                65

<210> SEQ ID NO 67
<211> LENGTH: 66
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 67
gaauacucaa gcuaugcauc caacgcguug ggagcucucc ggaucggcag aggagccaca    60
aagguu                                                               66

<210> SEQ ID NO 68
<211> LENGTH: 67
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 68
gaauacucaa gcuaugcauc caacgcguug ggagcucucc ggaucggcag aggagccaca    60
aagguuc                                                              67

<210> SEQ ID NO 69
<211> LENGTH: 68
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 69
gaauacucaa gcuaugcauc caacgcguug ggagcucucc ggaucggcag aggagccaca    60
aagguucc                                                             68

<210> SEQ ID NO 70
<211> LENGTH: 72
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 70
gaauacucaa gcuaugcauc caacgcguug ggagcucucc ggaucggcag aggagccaca    60
aagguuccac gc                                                        72

<210> SEQ ID NO 71
<211> LENGTH: 73
<212> TYPE: RNA
<213> ORGANISM: Artificial Sequence
<220> FEATURE:
<223> OTHER INFORMATION: Description of Artificial Sequence: antisense
``` nucleic acid against RNA originating from HBV

<400> SEQUENCE: 71
gaauacucaa gcuaugcauc caacgcguug ggagcucucc ggaucggcag aggagccaca    60
aagguuccac gca    73

<210> SEQ ID NO 72
<211> LENGTH: 74
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 72
gaauacucaa gcuaugcauc caacgcguug ggagcucucc ggaucggcag aggagccaca    60
aagguuccac gcau    74

<210> SEQ ID NO 73
<211> LENGTH: 75
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 73
gaauacucaa gcuaugcauc caacgcguug ggagcucucc ggaucggcag aggagccaca    60
aagguuccac gcaug    75

<210> SEQ ID NO 74
<211> LENGTH: 76
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 74
gaauacucaa gcuaugcauc caacgcguug ggagcucucc ggaucggcag aggagccaca    60
aagguuccac gcaugc    76

<210> SEQ ID NO 75
<211> LENGTH: 77
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 75
gaauacucaa gcuaugcauc caacgcguug ggagcucucc ggaucggcag aggagccaca    60
aagguuccac gcaugcg    77

<210> SEQ ID NO 76
<211> LENGTH: 102
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 76

```
gaauacucaa gcuaugcauc caacgcguug ggagcucucc ggaucggcag aggagccaca      60
aagguuccac gcaugcgcug auggccuaug gccaagcccc ag                        102

<210> SEQ ID NO 77
<211> LENGTH: 103
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 77
gaauacucaa gcuaugcauc caacgcguug ggagcucucc ggaucggcag aggagccaca      60
aagguuccac gcaugcgcug auggccuaug gccaagcccc agc                       103

<210> SEQ ID NO 78
<211> LENGTH: 104
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 78
gaauacucaa gcuaugcauc caacgcguug ggagcucucc ggaucggcag aggagccaca      60
aagguuccac gcaugcgcug auggccuaug gccaagcccc agcc                      104

<210> SEQ ID NO 79
<211> LENGTH: 105
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 79
gaauacucaa gcuaugcauc caacgcguug ggagcucucc ggaucggcag aggagccaca      60
aagguuccac gcaugcgcug auggccuaug gccaagcccc agcca                     105

<210> SEQ ID NO 80
<211> LENGTH: 106
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 80
gaauacucaa gcuaugcauc caacgcguug ggagcucucc ggaucggcag aggagccaca      60
aagguuccac gcaugcgcug auggccuaug gccaagcccc agccag                    106

<210> SEQ ID NO 81
<211> LENGTH: 107
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 81
gaauacucaa gcuaugcauc caacgcguug ggagcucucc ggaucggcag aggagccaca      60
aagguuccac gcaugcgcug auggccuaug gccaagcccc agccagu                   107
```

<210> SEQ ID NO 82
<211> LENGTH: 108
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 82
gaauacucaa gcuaugcauc caacgcguug ggagcucucc ggaucggcag aggagccaca    60
aagguuccac gcaugcgcug auggccuaug gccaagcccc agccagug             108

<210> SEQ ID NO 83
<211> LENGTH: 109
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 83
gaauacucaa gcuaugcauc caacgcguug ggagcucucc ggaucggcag aggagccaca    60
aagguuccac gcaugcgcug auggccuaug gccaagcccc agccagugg            109

<210> SEQ ID NO 84
<211> LENGTH: 110
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 84
gaauacucaa gcuaugcauc caacgcguug ggagcucucc ggaucggcag aggagccaca    60
aagguuccac gcaugcgcug auggccuaug gccaagcccc agccagugggg           110

<210> SEQ ID NO 85
<211> LENGTH: 111
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 85
gaauacucaa gcuaugcauc caacgcguug ggagcucucc ggaucggcag aggagccaca    60
aagguuccac gcaugcgcug auggccuaug gccaagcccc agccagugggg g         111

<210> SEQ ID NO 86
<211> LENGTH: 112
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 86
gaauacucaa gcuaugcauc caacgcguug ggagcucucc ggaucggcag aggagccaca    60
aagguuccac gcaugcgcug auggccuaug gccaagcccc agccagugggg gg        112

<210> SEQ ID NO 87
<211> LENGTH: 113
<212> TYPE: RNA

<213> ORGANISM: Artificial Sequence
<220> FEATURE:
<223> OTHER INFORMATION: Description of Artificial Sequence: antisense
      nucleic acid against RNA originating from HBV

<400> SEQUENCE: 87
gaauacucaa gcuaugcauc caacgcguug ggagcucucc ggaucggcag aggagccaca      60
aagguuccac gcaugcgcug auggccuaug gccaagcccc agccaguggg ggu            113

<210> SEQ ID NO 88
<211> LENGTH: 114
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 88
gaauacucaa gcuaugcauc caacgcguug ggagcucucc ggaucggcag aggagccaca      60
aagguuccac gcaugcgcug auggccuaug gccaagcccc agccaguggg gguu           114

<210> SEQ ID NO 89
<211> LENGTH: 115
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 89
gaauacucaa gcuaugcauc caacgcguug ggagcucucc ggaucggcag aggagccaca      60
aagguuccac gcaugcgcug auggccuaug gccaagcccc agccaguggg gguug          115

<210> SEQ ID NO 90
<211> LENGTH: 116
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 90
gaauacucaa gcuaugcauc caacgcguug ggagcucucc ggaucggcag aggagccaca      60
aagguuccac gcaugcgcug auggccuaug gccaagcccc agccaguggg gguugc         116

<210> SEQ ID NO 91
<211> LENGTH: 117
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 91
gaauacucaa gcuaugcauc caacgcguug ggagcucucc ggaucggcag aggagccaca      60
aagguuccac gcaugcgcug auggccuaug gccaagcccc agccaguggg gguugcg        117

<210> SEQ ID NO 92
<211> LENGTH: 118
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 92
gaauacucaa gcuaugcauc caacgcguug ggagcucucc ggaucggcag aggagccaca     60
aagguuccac gcaugcgcug auggccuaug gccaagcccc agccaguggg gguugcgu     118

<210> SEQ ID NO 93
<211> LENGTH: 135
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 93
gaauacucaa gcuaugcauc caacgcguug ggagcucucc ggaucggcag aggagccaca     60
aagguuccac gcaugcgcug auggccuaug gccaagcccc agccaguggg gguugcguca    120
gcaaacacuu ggcac                                                     135

<210> SEQ ID NO 94
<211> LENGTH: 136
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 94
gaauacucaa gcuaugcauc caacgcguug ggagcucucc ggaucggcag aggagccaca     60
aagguuccac gcaugcgcug auggccuaug gccaagcccc agccaguggg gguugcguca    120
gcaaacacuu ggcaca                                                    136

<210> SEQ ID NO 95
<211> LENGTH: 137
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 95
gaauacucaa gcuaugcauc caacgcguug ggagcucucc ggaucggcag aggagccaca     60
aagguuccac gcaugcgcug auggccuaug gccaagcccc agccaguggg gguugcguca    120
gcaaacacuu ggcacag                                                   137

<210> SEQ ID NO 96
<211> LENGTH: 138
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 96
gaauacucaa gcuaugcauc caacgcguug ggagcucucc ggaucggcag aggagccaca     60
aagguuccac gcaugcgcug auggccuaug gccaagcccc agccaguggg gguugcguca    120
gcaaacacuu ggcacaga                                                  138

<210> SEQ ID NO 97
<211> LENGTH: 139
<212> TYPE: RNA

```
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 97
gaauacucaa gcuaugcauc caacgcguug ggagcucucc ggaucggcag aggagccaca     60
aagguuccac gcaugcgcug auggccuaug gccaagcccc agccagugggg gguugcguca   120 gcaaacacuu ggcacagac                                                 139

<210> SEQ ID NO 98
<211> LENGTH: 140
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 98
gaauacucaa gcuaugcauc caacgcguug ggagcucucc ggaucggcag aggagccaca     60
aagguuccac gcaugcgcug auggccuaug gccaagcccc agccagugggg gguugcguca   120 gcaaacacuu ggcacagacc                                                140

<210> SEQ ID NO 99
<211> LENGTH: 141
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 99
gaauacucaa gcuaugcauc caacgcguug ggagcucucc ggaucggcag aggagccaca     60
aagguuccac gcaugcgcug auggccuaug gccaagcccc agccagugggg gguugcguca   120 gcaaacacuu ggcacagacc a                                              141

<210> SEQ ID NO 100
<211> LENGTH: 142
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 100
gaauacucaa gcuaugcauc caacgcguug ggagcucucc ggaucggcag aggagccaca     60
aagguuccac gcaugcgcug auggccuaug gccaagcccc agccagugggg gguugcguca   120 gcaaacacuu ggcacagacc ag                                             142

<210> SEQ ID NO 101
<211> LENGTH: 151
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 101
gaauacucaa gcuaugcauc caacgcguug ggagcucucc ggaucggcag aggagccaca     60
aagguuccac gcaugcgcug auggccuaug gccaagcccc agccagugggg gguugcguca   120
```

```
gcaaacacuu ggcacagacc aggccguugc c                                151
```

<210> SEQ ID NO 102
<211> LENGTH: 152
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 102

```
gaauacucaa gcuaugcauc caacgcguug ggagcucucc ggaucggcag aggagccaca    60
aagguuccac gcaugcgcug auggccuaug gccaagcccc agccagugggg gguugcguca  120
gcaaacacuu ggcacagacc aggccguugc cg                                152
```

<210> SEQ ID NO 103
<211> LENGTH: 153
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 103

```
gaauacucaa gcuaugcauc caacgcguug ggagcucucc ggaucggcag aggagccaca    60
aagguuccac gcaugcgcug auggccuaug gccaagcccc agccaguggg gguugcguca  120
gcaaacacuu ggcacagacc aggccguugc cga                               153
```

<210> SEQ ID NO 104
<211> LENGTH: 154
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 104

```
gaauacucaa gcuaugcauc caacgcguug ggagcucucc ggaucggcag aggagccaca    60
aagguuccac gcaugcgcug auggccuaug gccaagcccc agccaguggg gguugcguca  120
gcaaacacuu ggcacagacc aggccguugc cgag                              154
```

<210> SEQ ID NO 105
<211> LENGTH: 155
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 105

```
gaauacucaa gcuaugcauc caacgcguug ggagcucucc ggaucggcag aggagccaca    60
aagguuccac gcaugcgcug auggccuaug gccaagcccc agccaguggg gguugcguca  120
gcaaacacuu ggcacagacc aggccguugc cgagc                             155
```

<210> SEQ ID NO 106
<211> LENGTH: 156
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 106
gaauacucaa gcuaugcauc caacgcguug ggagcucucc ggaucggcag aggagccaca      60
aagguuccac gcaugcgcug auggccuaug gccaagcccc agccaguggg gguugcguca     120
gcaaacacuu ggcacagacc aggccguugc cgagca                               156

<210> SEQ ID NO 107
<211> LENGTH: 196
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 107
gaauacucaa gcuaugcauc caacgcguug ggagcucucc ggaucggcag aggagccaca      60
aagguuccac gcaugcgcug auggccuaug gccaagcccc agccaguggg gguugcguca     120
gcaaacacuu ggcacagacc aggccguugc cgagcaacgg gguaaagguu cauguacugu    180
uuacuuagaa aggccu                                                     196

<210> SEQ ID NO 108
<211> LENGTH: 197
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 108
gaauacucaa gcuaugcauc caacgcguug ggagcucucc ggaucggcag aggagccaca      60
aagguuccac gcaugcgcug auggccuaug gccaagcccc agccaguggg gguugcguca     120
gcaaacacuu ggcacagacc aggccguugc cgagcaacgg gguaaagguu cauguacugu    180
uuacuuagaa aggccuu                                                    197

<210> SEQ ID NO 109
<211> LENGTH: 198
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 109
gaauacucaa gcuaugcauc caacgcguug ggagcucucc ggaucggcag aggagccaca      60
aagguuccac gcaugcgcug auggccuaug gccaagcccc agccaguggg gguugcguca     120
gcaaacacuu ggcacagacc aggccguugc cgagcaacgg gguaaagguu cauguacugu    180
uuacuuagaa aggccuug                                                   198

<210> SEQ ID NO 110
<211> LENGTH: 199
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 110
gaauacucaa gcuaugcauc caacgcguug ggagcucucc ggaucggcag aggagccaca      60
aagguuccac gcaugcgcug auggccuaug gccaagcccc agccaguggg gguugcguca     120
gcaaacacuu ggcacagacc aggccguugc cgagcaacgg gguaaagguu cauguacugu        180
uuacuuagaa aggccuugu                                                    199

<210> SEQ ID NO 111
<211> LENGTH: 200
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 111
gaauacucaa gcuaugcauc caacgcguug ggagcucucc ggaucggcag aggagccaca        60
aagguuccac gcaugcgcug auggccuaug gccaagcccc agccaguggg gguugcguca       120
gcaaacacuu ggcacagacc aggccguugc cgagcaacgg gguaaagguu cauguacugu       180
uuacuuagaa aggccuugua                                                   200

<210> SEQ ID NO 112
<211> LENGTH: 201
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 112
gaauacucaa gcuaugcauc caacgcguug ggagcucucc ggaucggcag aggagccaca        60
aagguuccac gcaugcgcug auggccuaug gccaagcccc agccaguggg gguugcguca       120
gcaaacacuu ggcacagacc aggccguugc cgagcaacgg gguaaagguu cauguacugu       180
uuacuuagaa aggccuugua a                                                 201

<210> SEQ ID NO 113
<211> LENGTH: 202
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 113
gaauacucaa gcuaugcauc caacgcguug ggagcucucc ggaucggcag aggagccaca        60
aagguuccac gcaugcgcug auggccuaug gccaagcccc agccaguggg gguugcguca       120
gcaaacacuu ggcacagacc aggccguugc cgagcaacgg gguaaagguu cauguacugu       180
uuacuuagaa aggccuugua ag                                                202

<210> SEQ ID NO 114
<211> LENGTH: 203
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 114
gaauacucaa gcuaugcauc caacgcguug ggagcucucc ggaucggcag aggagccaca        60
aagguuccac gcaugcgcug auggccuaug gccaagcccc agccaguggg gguugcguca       120
gcaaacacuu ggcacagacc aggccguugc cgagcaacgg gguaaagguu cauguacugu       180
uuacuuagaa aggccuugua agu                                              203

<210> SEQ ID NO 115
<211> LENGTH: 204
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 115
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguu                                             204

<210> SEQ ID NO 116
<211> LENGTH: 242
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 116
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguuggcgag aaagugaaag ccuguuuagc uuguauacau      240
gc                                                                     242

<210> SEQ ID NO 117
<211> LENGTH: 256
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 117
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguuggcgag aaagugaaag ccuguuuagc uuguauacau      240
gcauacaaag gcauua                                                      256

<210> SEQ ID NO 118
<211> LENGTH: 267
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 118
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180

```
uuacuuagaa aggccuugua aguuggcgag aaagugaaag ccuguuuagc uuguauacau      240
gcauacaaag gcauuaaggc aggauau                                         267
```

<210> SEQ ID NO 119
<211> LENGTH: 293
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 119

```
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguuggcgag aaagugaaag ccuguuuagc uuguauacau      240
gcauacaaag gcauuaaggc aggauaucca cauuguguaa auggagcagc aaa             293
```

<210> SEQ ID NO 120
<211> LENGTH: 305
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 120

```
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguuggcgag aaagugaaag ccuguuuagc uuguauacau      240
gcauacaaag gcauuaaggc aggauaucca cauuguguaa auggagcagc aaagcccaaa      300
agacc                                                                 305
```

<210> SEQ ID NO 121
<211> LENGTH: 352
<212> TYPE: RNA
<213> ORGANISM: Artificial Sequence
<220> FEATURE:
<223> OTHER INFORMATION: Description of Artificial Sequence: antisense
      nucleic acid against RNA originating from HBV

<400> SEQUENCE: 121

```
gaauacucaa gcuaugcauc caacgcguug ggagcucucc ggaucggcag aggagccaca       60
aagguuccac gcaugcgcug auggccuaug gccaagcccc agccaguggg gguugcguca      120
gcaaacacuu ggcacagacc aggccguugc cgagcaacgg gguaaagguu cauguacugu      180
uuacuuagaa aggccuugua aguuggcgag aaagugaaag ccuguuuagc uuguauacau      240
gcauacaaag gcauuaaggc aggauaucca cauuguguaa auggagcagc aaagcccaaa      300
agacccacaa uucuuugaca uacuuuccaa ucaauaggcc uguuaacagg aa              352
```

ANTISENSE NUCLEIC ACIDS TARGETING HBV

The present application claims the benefit of priority from PCT Application Serial No. PCT/EP98/03632 (WO 98/58055) filed Jun. 16, 1998, and German Application Serial No. 197 25 803.4 filed Jun. 18, 1997.

The present invention concerns antisense nucleic acids, which are directed against specific sequences of RNA molecules originated from HBV, and vectors and host cells containing these antisense nucleic acids.

Chronic infections with the hepatitis-B virus (HBV) play a central role in the pathogenesis of liver cell carcinoma in humans. Hepadna viruses, of which HBV is one, replicate their DNA genome through reverse transcription of an RNA intermediate, the so-called pregenomic RNA. The application of antisense inhibitors represents, in a particularly specific manner, a therapeutic possibility for HBV infection. The inhibition of the propagation of the HBV can take place with the help of the antisense strategy both through inhibition of reverse transcription, with pregenomic RNA as the target, as well as through blocking of translation, with viral mRNAs as targets. Pregenomic RNA represents the most reasonable RNA target since it is the earliest target for an antisense nucleic acid in the replication cycle of the virus.

In the past, HBV-directed antisense sequences were directed arbitrarily in particular against 5' regions of viral mRNAs, their cap structure, or the polyadenylation signal (Goodarzi et al., J. Gen. Viro. 71: 3021–3025 (1990); Blum et al., Lancet 337: 1230 (1991); Wu, G. Y. and Wu C. H., J. Biol. Chem. 267: 12436–12439 (1992); Reinis et al., Folia Biol. (Praha) 39: 262–269 (1993); Yao et al., Zhanghua Yi Xue Za Zhi 74: 74–76 (1994); Yao et al., Acta Virol. 39: 227–230 (1995); Yao et al., J. Virol. Hepat. 2: 85–89 (1995); Moriya et al., Biochem. Biophys. Res. Comm. 278: 217–223 (1996)).

Since the selection of the antisense sequences in the past has been rather arbitrary and without rational selection criteria, a large part of the sequences investigated were not effective. Important influence variables on the association behavior between the antisense nucleic acid and the target RNA, such as, for example, the accessibility of the target RNAs to the antisense nucleic acids, were not considered. Furthermore, the structural diversity of the antisense RNAs was not considered and thus the potential of effective antisense inhibitors was not exhausted.

Thus the present invention is based on the object of preparing antisense nucleic acids which hybridize particularly effectively with the pregenomic RNA of human HBV in particular.

This object is realized through the embodiments characterized in the attached patent claims. In particular, an antisense nucleic acid is prepared which is directed against a specific sequence of an RNA molecule originating from HBV as target molecule with the antisense nucleic acid being smaller than the RNA molecule and having an association constant k of at least $5 \times 10^3$ $M^{-1}s^{-1}$. Preferably the association constant k is at least $2 \times 10^4$ $M^{-1}s^{-1}$.

The concept "antisense nucleic acid" means a native, semi-synthetic, synthetic, or modified nucleic acid molecule of deoxyribonucleotides and/or ribonucleotides and/or modified nucleotides.

The RNA molecule originating from HBV can be pregenomic RNA, pre-C mRNA, pre-S1 mRNA, pre-S2/S mRNA, or the transcript of the X gene. Preferably the RNA molecule is the pregenomic RNA of HBV. Pre-C mRNA is an RNA transcript initiated at the precore initiation codon of the C gene encoding the nucleopsid protein of HBV. Pre-S1 mRNA is an RNA transcript initiated at the pre-S1 initiation codon of the S gene encoding the "major" envelope protein HbsAg of HBV. Pre-S1 mRNA is an RNA transcript initiated at the second, or S1, initiation codon of the S gene encoding the "major" envelope protein of HbsAg of HBV. See Fauci et al., ed. Harrison's Principles of Internal Medicine, McGraw-Hill, $14^{th}$ Ed. Pp. 1677–1678.

In a preferred embodiment of the present invention, the antisense nucleic acid contains the antisense oligodeoxynucleotide designated with SEQ ID No. 1 to 3. In another preferred embodiment of the present invention, the antisense nucleic acid contains the antisense ribonucleic acid sequences designated with SEQ ID No. 4 through 121 which rapidly hybridize with the pregenomic RNA.

The preferred antisense nucleic acid sequences, designated with SEQ ID No. 1 through 121, hybridize in vitro with above-average rapidity with the pregenomic RNA and are therefore excellent inhibitors of HBV replication in vivo. Surprisingly it was found that these preferred antisense nucleic acids have a selectivity with respect to pregenomic RNA of HBV even if identical target sequence regions occur on the mRNAs of HBV.

A further object of the present invention is a vector which contains the above defined antisense nucleic acid according to the invention or which contains a corresponding DNA sequence complementary to the antisense nucleic acid which following transcription in suitable host cells results in the above-defined antisense nucleic acid according to the invention. The vector according to the invention can preferably contain suitable regulatory elements such as promoters, enhancers, and termination sequences. In an embodiment according to the invention, the vector can be used, for example, for stable integration of the nucleic acid according to the invention into the genetic material of a host cell.

A further object of the present invention is a host cell which contains the antisense nucleic acid or the vector according to the invention. Suitable host cells are, for example, all mammalian cells which carry sequences of hepatitis viruses, preferably human cells which carry hepatitis B virus sequences.

A further object of the present invention is a medication which contains the antisense nucleic acid or the vector according to the invention, possibly in a pharmaceutically acceptable base and/or diluting agent. The medication according to the invention can be used to inhibit or eliminate disease conditions caused by HBV infections through transient or stable integration of the antisense nucleic acid according to the invention by transformation and/or transfection in host cells infected with HBV.

EXAMPLE

Figure 1:
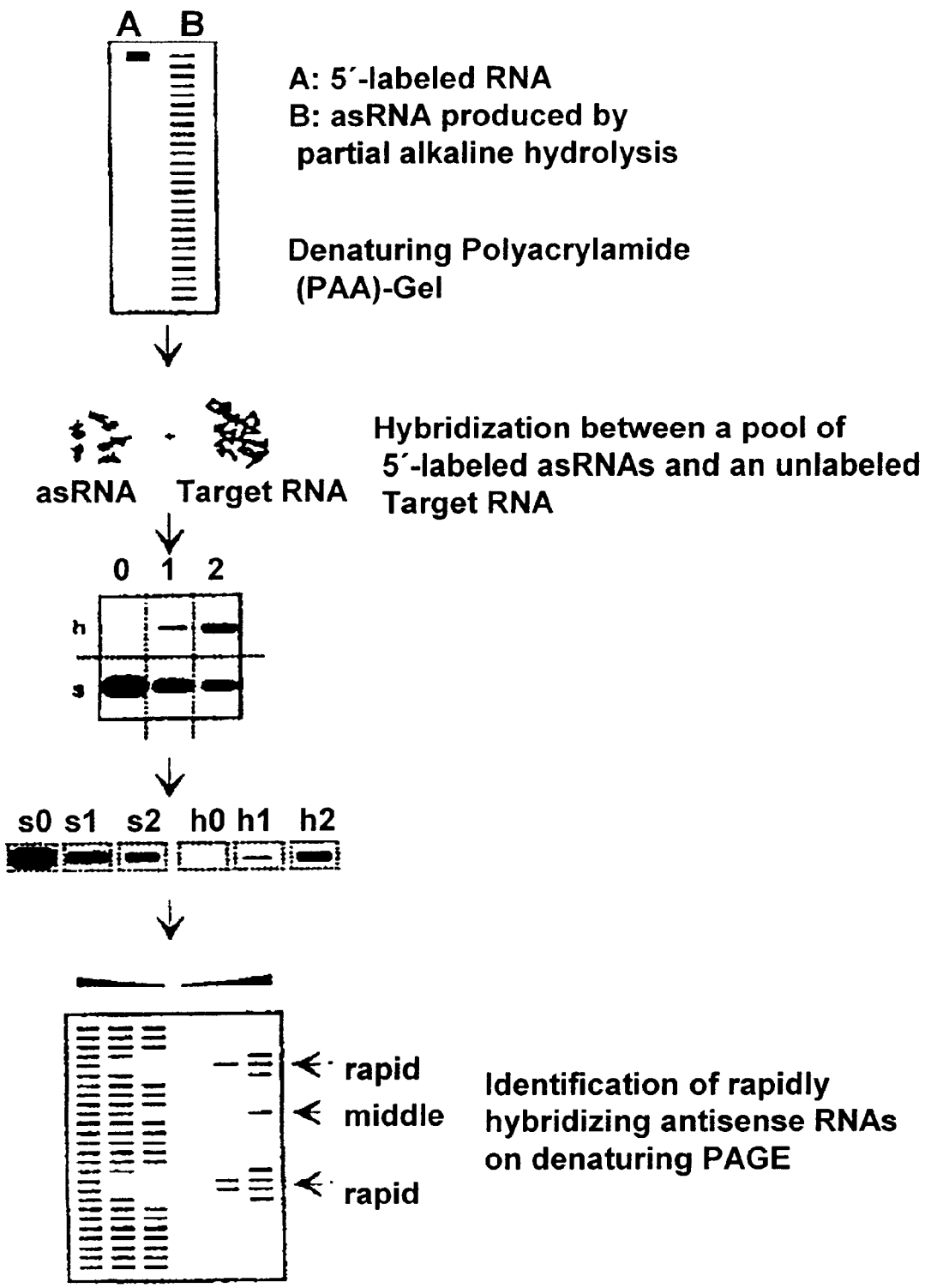
FIG. 1 is a schematic representation of the in vitro selection tests and the identification of rapidly hybridizing antisense RNA molecules.

Plasmids for the In Vitro Synthesis of Antisense RNAs and Target RNA

Conventionally obtainable, cloned HBVadw2-DNA was cleaved with the restriction enzyme Sau3Al and the restriction fragments were cloned in the BamH1 cleavage site of the transcription vector pGEM-7Zf+(Promega) and confirmed through the DNA sequencing. Two of these clones, pSau3 and pSau5-1, contained strands of HBVadw2 (pSau3: 334 nucleotide, positions 944–1266; pSau5-1: 260 nucleotides, positions 29–288) in antisense orientation with respect to the SP6 promoter. The derived antisense RNAs (Sau3 and Sau5-1) of these constructs contain additional polylinker sequences at their 5' ends (41 nucleotides) and their 3' ends (6 nucleotides). The RNA strand which contains the complementary sequences of Sau3' and Sau5-1 was transcribed in vitro using the SP5-RNA polymerase. The sense transcript contains 3320 of 3321 nucleotides of the pregenomic RNA (positions 2–3321) and additional unspecific sequences at the 5' end (3 nucleotides) and at the 3' end (209 nucleotides).

In Vitro Transcription of RNA

The plasmids were linearized prior to the in vitro transcription by the following enzymes: pSau3 and pSau5-1 by HindIII, PSP6HBV by PvuII. SP5-RNA-polymerase (Boehringer Mannheim) was used for in vitro transcription. 5 $\mu$g each of linearized template RNA was incubated in a reaction buffer which contained 40 mM tris-HCl, pH 8.0 (20° C.), 6 mM $MgCl_2$, 10 mM DTT, and 2 mM spermidin, in a total volume of 200 $\mu$l at 37° C. for 90 min. The reaction was started through addition of 20 U T7 RNA polymerase and was halted through addition of 10 mM $MgSO_4$ and 20 U DNaseI (Rnass-free, Boehringer Mannheim). After an additional incubation for 15 min at 37° C., the DNaseI decomposition was halted through addition of 25 mM EDTA. The RNAs were purified through gel filtration (Sephadex G50 medium, Pharmacia), phenol extraction, and ethanol precipitation.

$^{32}$P Labeling of RNAs

The 5' ends of the in vitro transcribed antisense RNA molecules (10 ng) were $^{32}$P-marked with phosphatase from calf intestine and with 100 $\mu$Ci [$\gamma$-32F]-ATP (10.0 mCi/mi, 3000 Ci/mmol) and polynucleotide kinase (Boehringer Mannheim) according to the methods known in the state of the art.

Alkaline Hydrolysis of Antisense RNA Molecules

For generation of a variable pool of HBV-directed antisense RNA molecules, $^{32}$P-5'-labeled original RNA was successively shortened through limited alkaline hydrolysis according to methods known in the state of the art. In this process, 2.5 pmol 5'-labeled RNA molecules in TE buffer (10 mM Tris/HCl, pH 8.0, 1 mM EDTA) was heated with 1.5 volumes of 0.5 mM $NaHCO_3$ to 96° C. for 8–10 min and then cooled on ice and desalted through gel filtration (sephadex G-50 fine, Pharmacia). After ethanol precipitation, the RNA molecules were dissolved in TE buffer. Following this the variable mixture of RNA molecules was heated for 10 min to 75° C. and was slowly cooled to 37° C. before use in hybridization tests in order to obtain a native folding of the RNA molecules.

Kinetic In Vitro Selection Method for Selective Identification of Rapidly-Hybridizing Antisense RNA Molecules The experimental process is described in the state of the art and is schematically represented in FIG. 1. 5'-labeled and partially hydrolyzed RNA was incubated with a ten or twenty fold molar excess (25 or 50 pmol, conditions of pseudofirst reaction order) of HBV pregenomic RNA in an end volume of 60 $\mu$l and with approximately physiological salt conditions (100 mM NaCl, 20 mM Tris/HCl, pH 7.4 and 10 mM $MgCl_2$) at 37° C. in order to favor the selection of physiologically active molecules. During the hybridization, aliquots of the reaction mixture were removed at various points in time and were introduced into ten volumes of precooled stop buffer (7 M urea, 20 mM Tris/HCl, pH 8.0, 10 mM EDTA, 0.5% SDS, 0.04% bromophenol blue, 0.04% xylene cyanol). After separation by means of native agarose-gel electrophoresis (0.8% agarose, TBE) the single-strand RNA molecules and the double-strand RNAs formed were cut from the gel and were recovered through centrifuging the gel pieces according to the "freeze-thaw method" (liquid nitrogen/37° C.). After the phenol treatment and ethanol precipitation, the RNA was dissolved in stop buffer and the single-strand as well as hybridized fractions were analyzed by means of denaturing PAGE (10% PAA, 7 M urea, TBE). The gels were dried and exposed to an x-ray film or a phosphorimager screen for further computer-aided quantitative analysis.

Determination of the Association Constants of Individual Antisense RNA Molecules For the quantitative analysis of the band intensities, the dried PAA gels were tested using a phosphorimager (Molecular Dynamics). Using the program "Image Quant" (Molecular Dynamics), the band intensities were measured and the data was transferred to the program "EXCEL" (Microsoft). For individual RNA molecules, the band intensities were entered on the time axis and a curve for an individual exponential decomposition was fitted through non-linear regression using the program "GRAFIT" (Erithacus Software, London, Great Britain). By plotting the calculated association constants (calculation based on the conditions of the pseudofirst reaction order) against the length of the antisense RNA molecules, different groups of rapidly hybridizing antisense RNA molecules were detected.

Antisense RNA, Directed Against the Pregenomic RNA of Human HBV Type adw2

Two original antisense RNA molecules which are directed against different regions of the pregenomic RNA of HBV were selected for performing an in vitro selection test. The first target area, positions 29–288, which is sequence homologous with regions of the 5' ends of the preS1 and preS2/S mRNAs, was already known as an effective target of antisense nucleic acids and was selected as a result of its high folding energy of the RNA secondary structure. The second target area, positions 933–1266, was selected on the basis of its sequence homology with the 5' end of the X gene transcript. The pregenomic RNA is approximately 10 times longer than these two antisense RNA molecules. As a result, the single-strand fraction can be separated in the course of the in vitro selection test from the double-strand fraction.

Kinetic Selection and Identification of Rapidly Binding Complementary RNA

Figure 2:
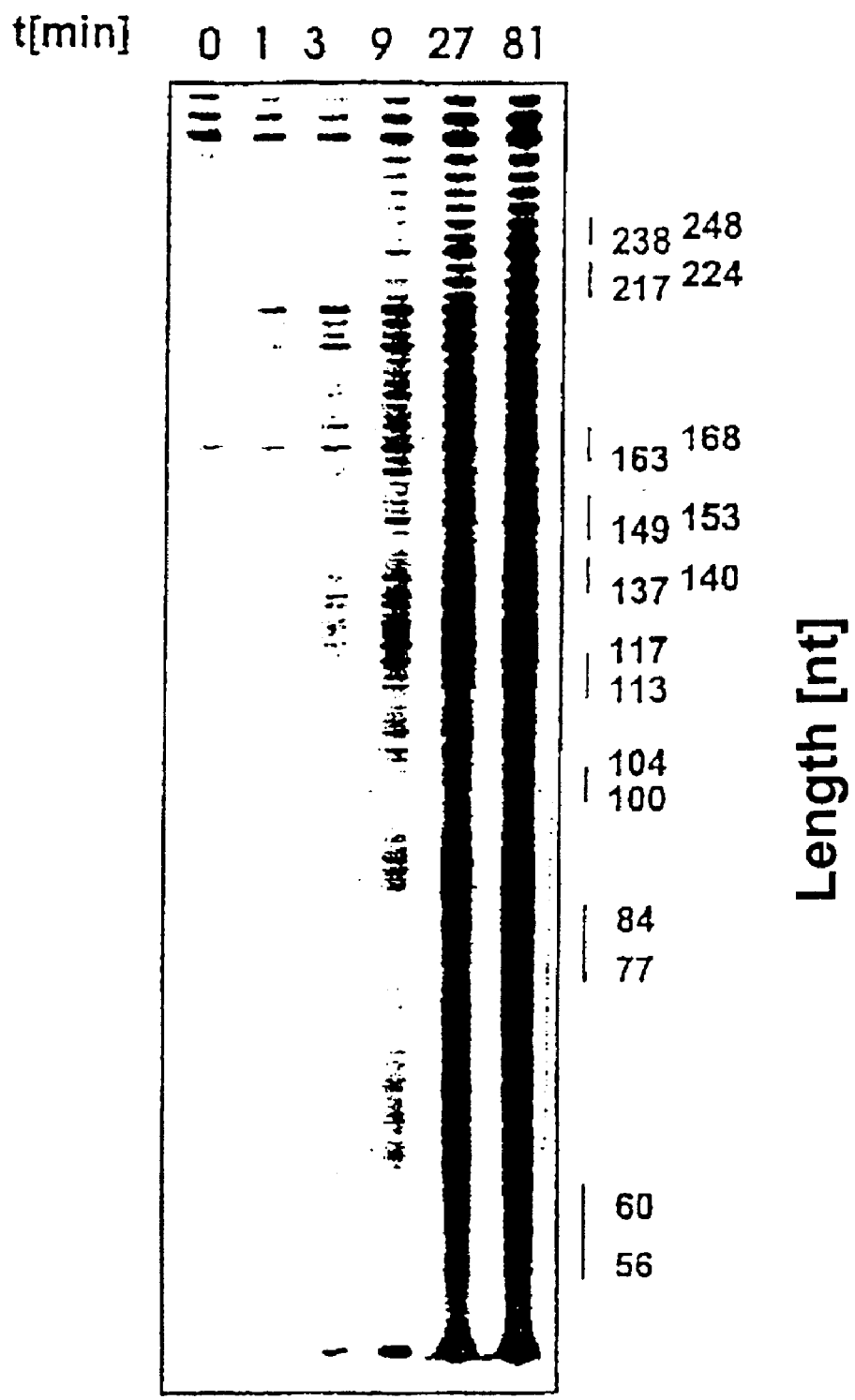
FIG. 2 is a photographic representation of an autoradiograph which shows the identification of Sau5-1 derived, rapidly hybridizing antisense RNA molecules.
Figure 3:
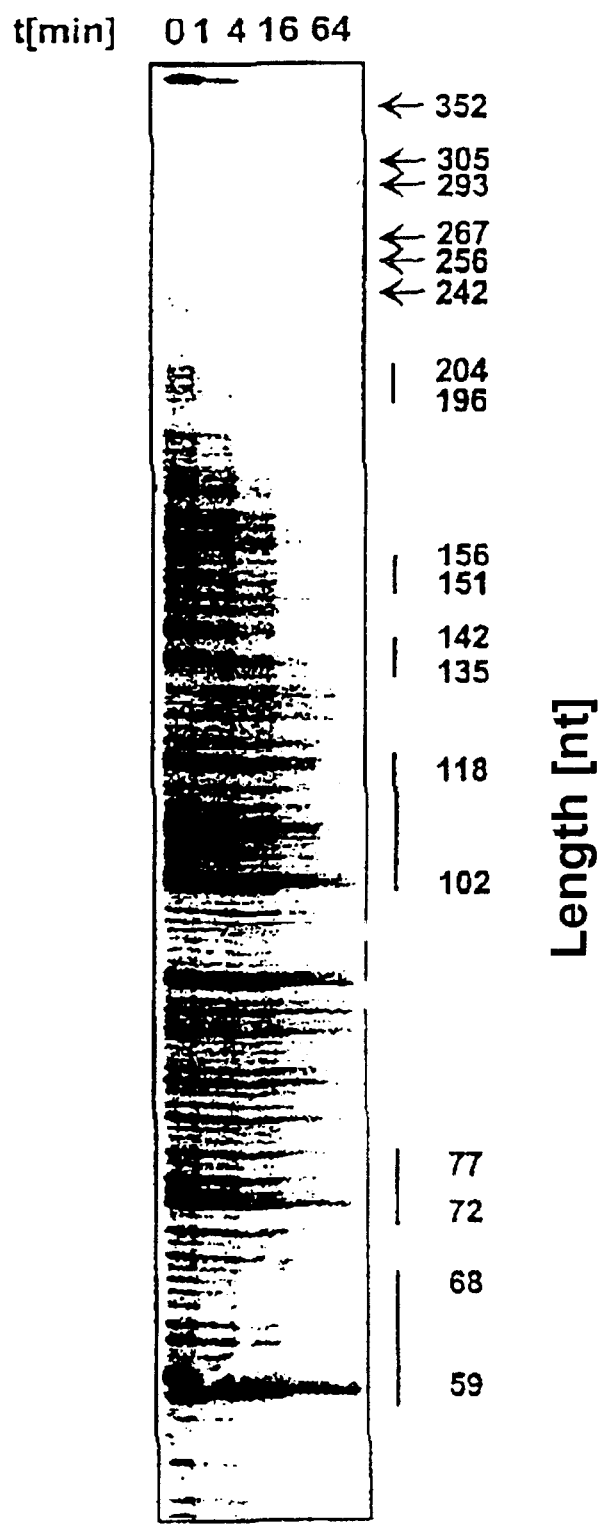
FIG. 3 is a photographic representation of an autoradiograph which shows the identification of Sau3 derived, rapidly hybridizing antisense RNA molecules.
Figure 4:
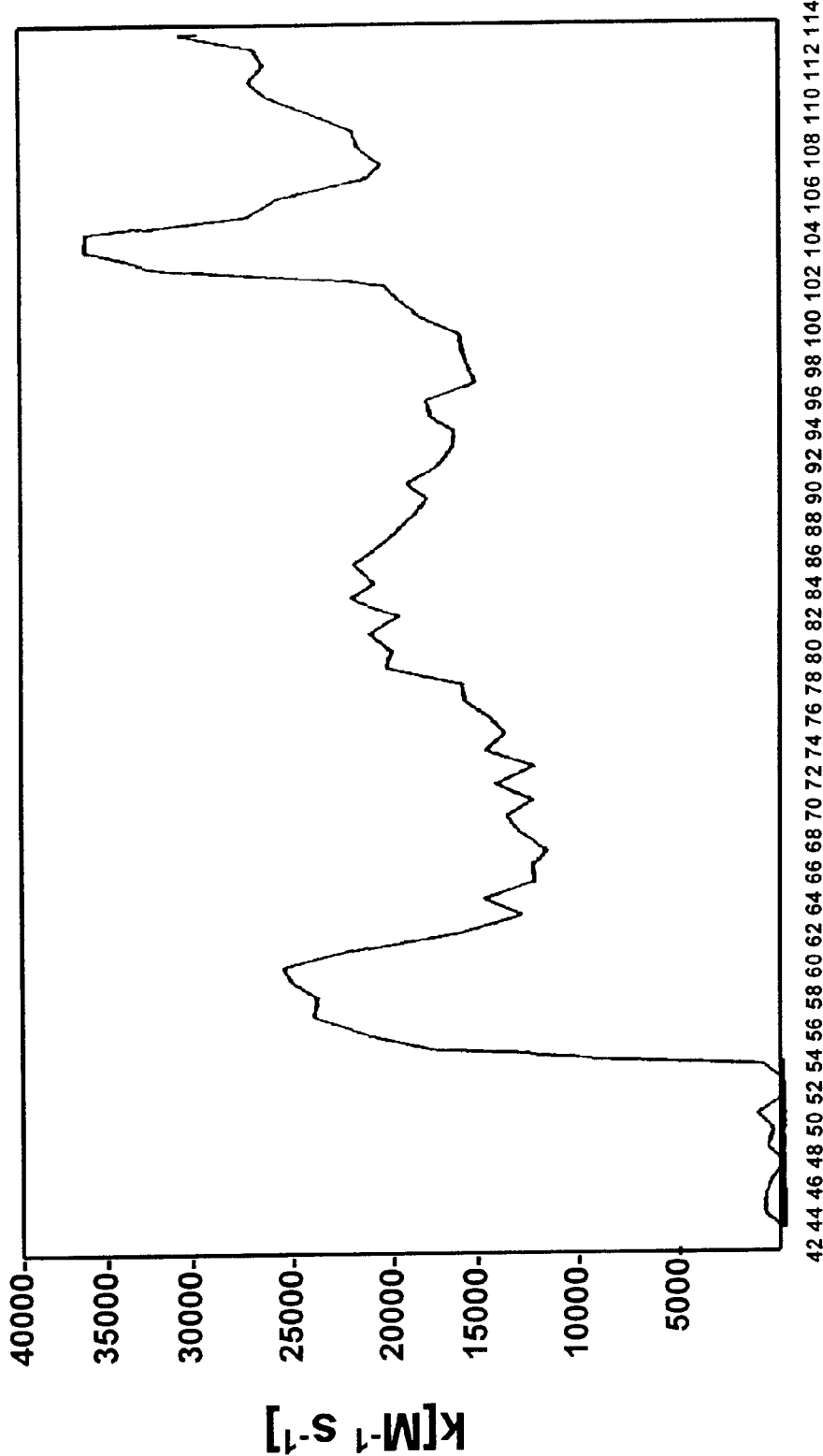
FIG. 4 is a graphic representation which shows the chain-length dependence of the association constants of Sau5-1 derived antisense RNA molecules.
Figure 5:
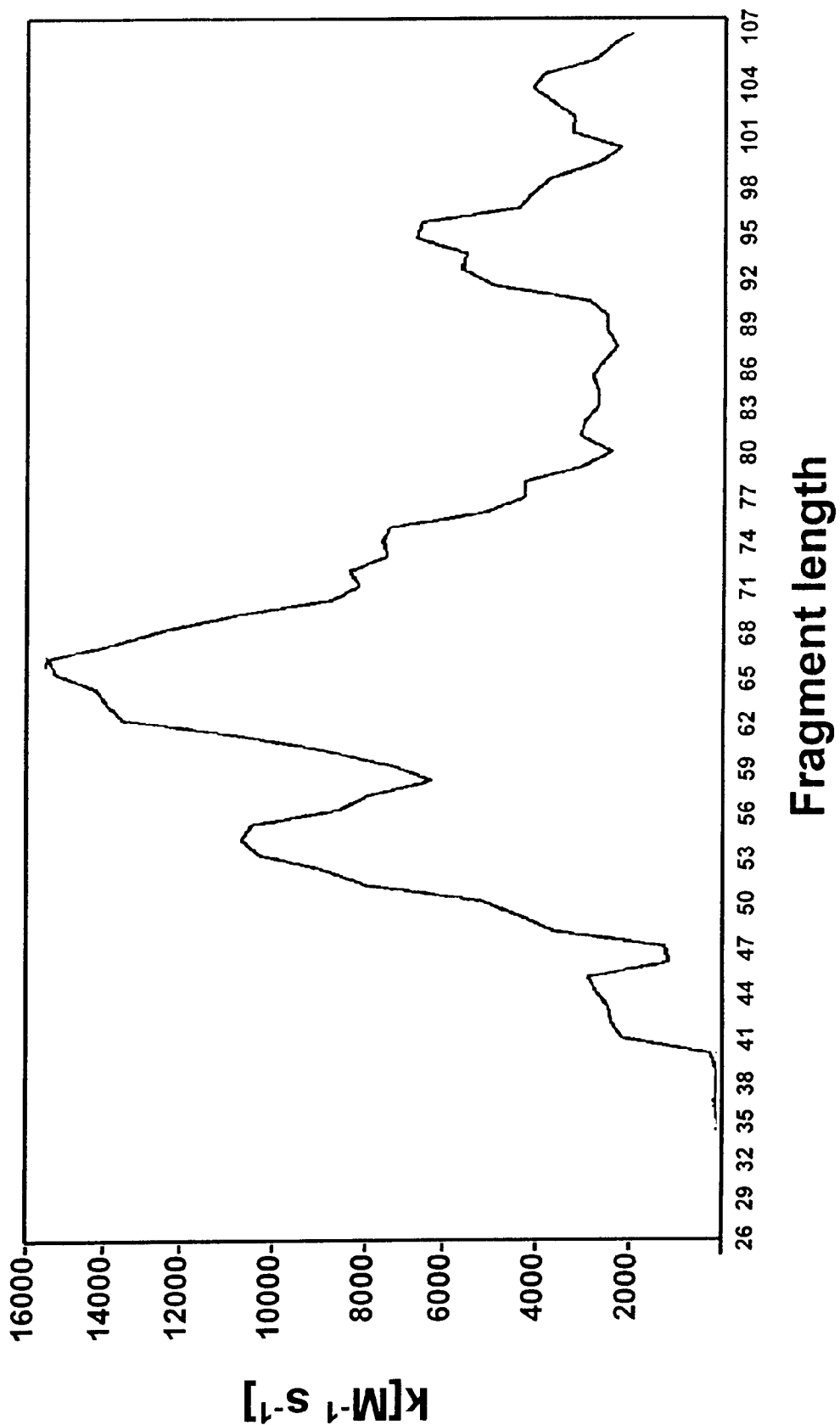
FIG. 5 is a graphic representation which shows the chain-length dependence of the association constants of Sau3 derived antisense RNA molecules.

The original antisense RNAs were synthesized through in vitro transcription and $^{32}$P labeling at the 5' end. Limited alkaline hydrolysis resulted in a pool of antisense RNA molecules which had the 5' end in common, but had a successively shortened 3' end. The association constant for these molecules was measured at 37° C. and physiologic ion concentration. The in vitro selection and identification of rapidly hybridizing antisense RNA molecules is schematically depicted in FIG. 1. The rapidly hybridizing molecules are the first which disappear from the trace of single-strand fraction and can be detected through their chain length. The experimental identification of rapidly binding, complementary RNA molecules is shown in FIGS. 2 and 3. The association constants, in relation to the chain length of related molecules which stem from one of the two original antisense constructs, are shown in FIGS. 4 and 5. The maximum association constants reach values of 2 to $4\times10^4$ $M^{-1}s^{-1}$, and even for relatively small antisense RNA molecules, they are higher than for the original full-length RNA and 3 times higher than the average of all association constants of either of the initial pools.

Accessibility of the Target RNA; Computer-Supported Prediction of the Secondary Structure of the Target RNA The complete secondary structure of the pregenomic RNA was predetermined using the program "MFold" (HUSAR: Heidelberg Unix Sequence Analysis Resources). The results of the in vitro selection experiments agree with the accessibility of the target RNA. Thus DNA oligonucleotide analogs were obtained from short selected antisense RNA molecules and were studied in transient in vivo replication tests.

What is claimed is:

1. An antisense nucleic acid complementary to an RNA molecule derived from a hepatitis B virus, wherein the nucleic acid has an association constant of at least $5 \times 10^3$ $M^{-1}$ $s^{-1}$ and is capable of reducing the expression of a hepatitis B virus polvpeptide in an infected cell, and wherein the antisense nucleic acid is selected from the group consisting of SEQ ID NOS: 1–3.

2. A vector assentially comprising a nucleic acid sequence complenentary to the antisense nucleic asid of claim 1.

* * * * *